United States Patent
Cernasov

(10) Patent No.: US 7,813,810 B2
(45) Date of Patent: Oct. 12, 2010

(54) APPARATUS AND METHOD FOR SUPPLYING POWER TO SUBCUTANEOUSLY IMPLANTED DEVICES

(76) Inventor: Andre N. Cernasov, 86 Miller La., Ringwood, NJ (US) 07456

( * ) Notice: Subject to any disclaimer, the term of this patent is extended or adjusted under 35 U.S.C. 154(b) by 925 days.

(21) Appl. No.: 11/622,969

(22) Filed: Jan. 12, 2007

(65) Prior Publication Data

US 2007/0167988 A1    Jul. 19, 2007

Related U.S. Application Data

(60) Provisional application No. 60/758,611, filed on Jan. 13, 2006.

(51) Int. Cl.
*A61N 1/00*    (2006.01)
(52) U.S. Cl. ........................................ 607/61
(58) Field of Classification Search ................. 607/61
See application file for complete search history.

(56) References Cited

U.S. PATENT DOCUMENTS 6,131,581 A * 10/2000 Leysieffer et al. .......... 128/899
6,491,647 B1  12/2002 Bridger et al.
6,809,462 B2 * 10/2004 Pelrine et al. ............... 310/319
2002/0103425 A1 * 8/2002 Mault ......................... 600/373
2002/0177782 A1  11/2002 Penner
2004/0230090 A1  11/2004 Hegde et al.

OTHER PUBLICATIONS

International Search Report of Application No. PCT-US07-00860 mailed Mar. 28, 2008.

* cited by examiner

*Primary Examiner*—George Manuel
*Assistant Examiner*—Shubatra Narayanaswamy
(74) *Attorney, Agent, or Firm*—Lowe Hauptman Ham & Berner, LLP

(57) ABSTRACT

A power source providing electric power to subcutaneously implanted devices capture mechanical energy from the expansion and contraction of a cross-section of a blood vessel during a systolic-diastolic blood pressure cycle include a mechano-electric transducer assembly mechanically coupled to involuntarily moving tissue. The transducer includes a deformable inner element and a substantially rigid outer structure positioned outward of the elastic inner element. A transducer element disposed between the substantially rigid outer structure and the inner element is operable to generate electric energy and output the electric energy to a pair of output terminals. A deformable biocompatible envelope substantially surrounds the outer structure, the inner element and the transducer element.

22 Claims, 13 Drawing Sheets

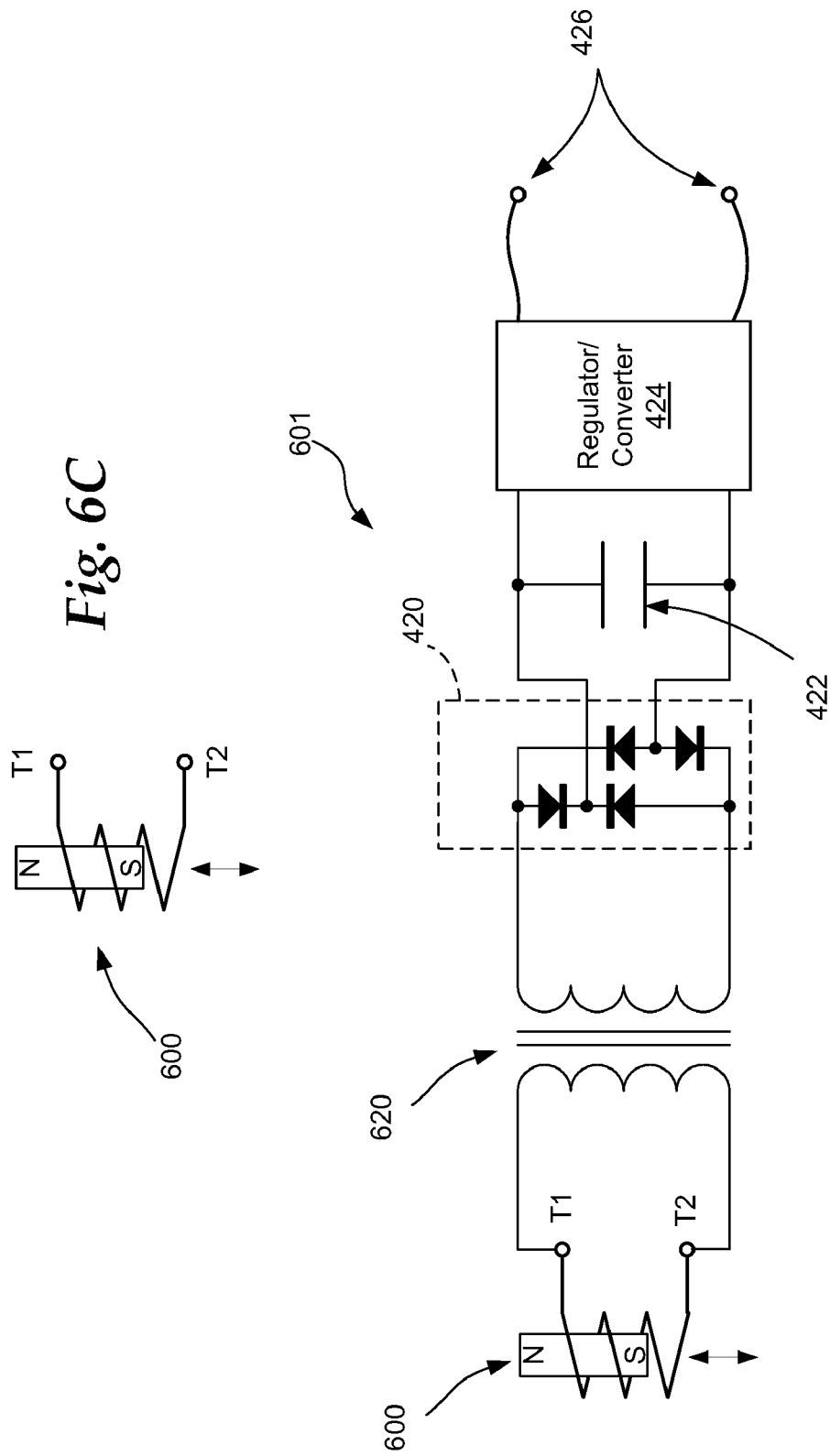

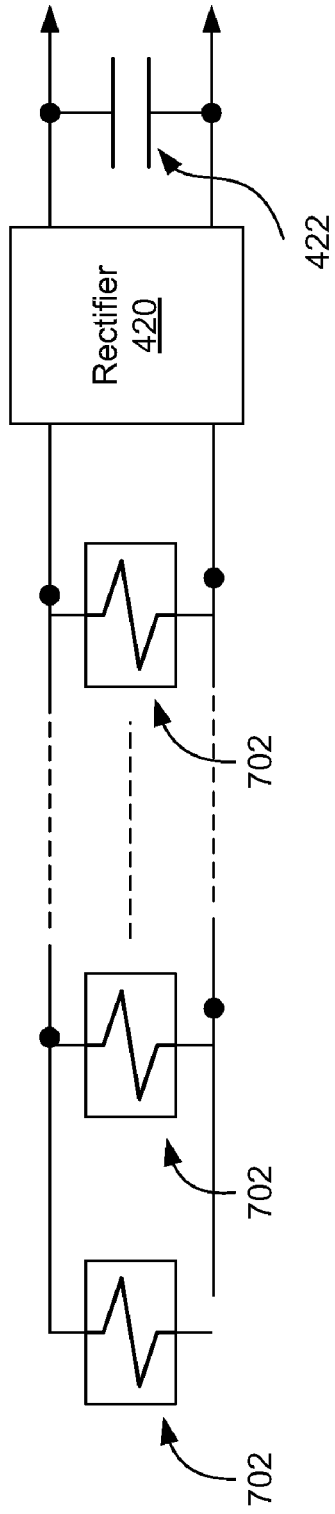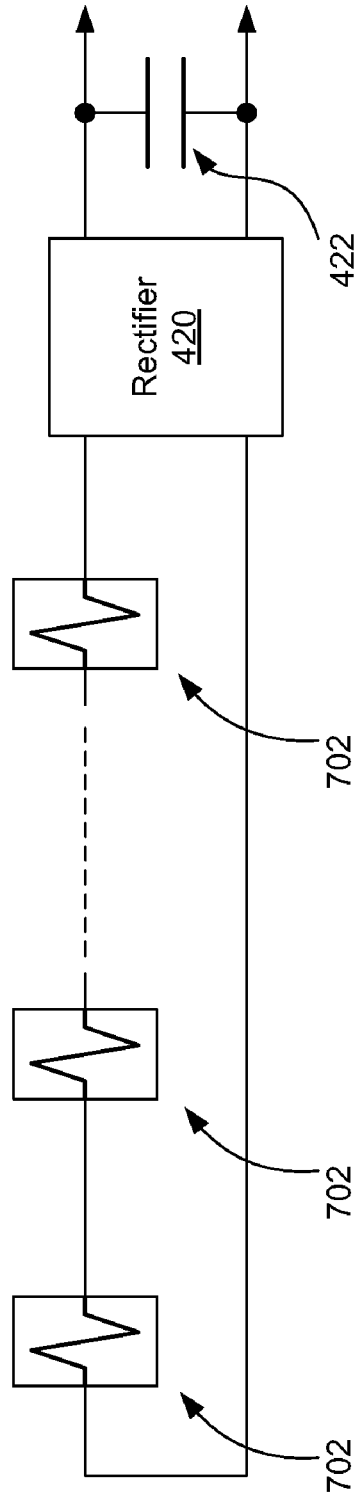

APPARATUS AND METHOD FOR SUPPLYING POWER TO SUBCUTANEOUSLY IMPLANTED DEVICES

CROSS-REFERENCE TO RELATED APPLICATION

This application claims the benefit of U.S. Provisional Patent Application Ser. No. 60/758,611 filed Jan. 13, 2006 entitled "Apparatus and Method for Supplying Electric Power to Implantable Medical Devices," and hereby incorporated by reference in its entirety.

BACKGROUND

The present disclosure relates to methods and apparatus for converting mechanical power into electrical power. More particularly, the invention relates to devices and methods that convert mechanical power of an intermittent pressure exerted by a flexible pipe or vessel, such as a blood vessel within a living body, into electrical power.

The operation of various subcutaneously implantable medical devices such as cardioverter-defibrillators, cardiac pacemakers, neurostimulators, medical monitoring devices and drug infusion devices requires electrical power typically provided by long life stored energy systems such as Lithium Iodine ($Li/I_2$), Lithium Silver Vanadium Oxide (Li/SVO), and Lithium Carbon Monofluoride (Li/CFx) batteries. The voltages provided are substantially constant over a period ranging typically from a few months to a few years and are available using current electronic technologies. For example a typical conventional Lithium Iodine battery used in a cardiac pacemaker device may provide a voltage between 2.5 and 3.3 volts and a current of a few microamperes for a period of 6 to 10 years.

Batteries for different implantable applications may have different characteristics. For example, a lithium silver vanadium oxide battery may be able to support the high current bursts of a few amperes required by an implantable cardioverter defibrillator. The Lithium Iodine and Lithium Carbon Monofluoride batteries are more suited for use in cardiac pacemakers, neurostimulators, and drug infusion devices where the electrical load ranges from microamperes to milliamperes.

Conventional power systems for implantable medical devices are not permanent in the sense that once the amount of stored energy diminishes below a certain acceptable level they need to be replaced with a new power system. The procedure to replace the power system typically requires surgery.

The size of the power system is a major determinant of the size of the implantable medical device it powers in the sense that the size of the power system may comprise one third to one half of the size of the implantable medical device. Since it is desirable for the well being of the patient to minimize the number of required surgical procedures, the size of the implanted power system must be sufficient to provide energy to the implantable medical device for as long of a period as possible.

The period between surgeries is then related to the storage ability of the technology used by the power system and the power requirements of the implantable medical device. The size of the implantable medical device is then related to the level of the power system and electronics technologies available at the time of the device implantation. For example, today the smallest pacemaker devices may be 1.5" in diameter and 0.3" thick. Other implantable medical devices may be considerably larger.

Furthermore, a new class of implantable medical devices comprises in-vivo medical monitoring devices requiring reliable long term power systems. Examples of long term in-vivo medical monitoring devices include, for example, implantable glucose monitoring devices and implantable blood pressure monitoring devices.

Sometimes it is common for a patient to require more that one implantable medical device. For example, a paraplegic patient may require multiple neurostimulant devices and a pacemaker or defibrillator device or an implantable insulin pump. The use of multiple implantable medical devices is expected to increase with the development of new smaller size medical devices based on micro-electro-mechanical-systems (MEMS) and bionanotechnology systems.

Therefore, in many applications it may be desirable to power an implantable medical device with a power system that is permanent in the sense that in normal operation it does not require maintenance or replacement. Such a permanent power system may not require surgery or other procedure that brings risk to the patient.

It may also be desirable for a power system for implantable medical devices to be of very small size, for example, small enough to be part of an implantable medical device that can be attached to a significant artery or vein. By means of example, an implantable medical monitoring device may use such a power system to monitor the blood pressure in an artery or vein.

SUMMARY

Methods and apparatus for supplying electric power to subcutaneously implanted devices may supply a substantially constant voltage for an unlimited period of time to local implantable medical devices, such as, for example, pacemakers, defibrillators, neurostimulators, drug delivery systems, and in-vivo medical monitoring devices.

One aspect of a method for supplying imbedded medical devices with electric power comprises generating electrical power by converting an involuntary mechanical movement of subcutaneous biological tissue into electricity. In one aspect, the involuntary mechanical movement of biological tissue comprises an expansion and contraction of blood vessels during systolic-diastolic cycles.

Another aspect includes coupling at least a portion of an apparatus configured to perform the above method to moving in-vivo tissues, converting mechanical energy from the relative motion between the moving tissues and the coupled portion of the apparatus to electricity using mechano-electric conversion techniques.

One aspect of such an apparatus may comprise one or more mechano-electric transducers having one or more mechanical inputs connected to in-vivo biological sources of relative involuntary mechanical movement and an electric output connected to an implantable medical device load.

One aspect of a device implementing the above disclosed method includes at least one mechano-electric transducer assembly mechanically coupled to involuntarily moving tissue. The mechano-electric transducer assembly includes a substantially rigid outer structure, a deformable inner element, and a mechano-electric transducer element disposed between the substantially rigid outer structure and the deformable inner element.

In addition, a deformable biocompatible envelope substantially surrounds the outer structure, the inner element and the mechano-electric transducer element. Furthermore, the deformable inner element is configured to apply a minimum pressure on a substantially surrounded blood vessel during a diastolic period and to move outward towards the outer structure during a systolic period, the expansion of the inner element operable to cause the mechano-electric transducer element to generate electricity.

Furthermore, in some aspects, the relative movements among different parts of the power system coupled to different in-vivo tissues alters the shape of a piezoelectric or piezomagnetic assembly that converts mechanical stress energy into electrical energy.

In other aspects, the relative mechanical movements of different parts of the power system coupled to a plurality of different in-vivo tissues alters the geometry of electric or magnetic energy storage elements, e.g., capacitors and inductors, creating energy flows derived from the relative mechanical movements of the different parts of the power system.

BRIEF DESCRIPTION OF THE DRAWINGS

The present invention is illustrated by way of example, and not by limitation, in the figures of the accompanying drawings, wherein elements having the same reference numeral designations represent like elements throughout and wherein:

FIG. 6C is a schematic illustrating the exemplary mechano-electric transducer shown in FIGS. 6A and 6B;

FIG. 6D is a schematic representation of an exemplary circuit employing the exemplary mechano-electric transducer shown in FIGS. 6A and 6B;

FIGS. 7A, 7B and 7C are schematics illustrating a mechano-electric transducer according to the invention.

DETAILED DESCRIPTION

Methods and apparatus for supplying electric power to subcutaneously implanted devices include converting mechanical energy from a local in-vivo environment, e.g., moving tissue engaged in voluntary or involuntary mechanical motion, into electrical energy. In particular, a subcutaneous power source is operable to convert part of the energy imparted by the heart muscle to the circulatory system into electrical energy.

Mechanical motion is generated by the voluntary or involuntary contraction of muscles or systems of muscles. Muscles engaged in involuntary mechanical motion include heart muscles, diaphragm, intercostals muscles and other muscles. Muscles engaged in voluntary mechanical motion include skeletal muscles and other muscles. A subcutaneous power source is operable to convert some of the mechanical energy imparted by these muscles into electric energy in order to operate implanted medical devices, such as, cardioverter-defibrillators, cardiac pacemakers, neurostimulators, medical monitoring devices, and drug infusion devices.

Conversion of the mechanical energy into electrical energy is performed by mechano-electric transducers based on, but not limited to, piezoelectric, electric and electromagnetic effects.

Figure 1:
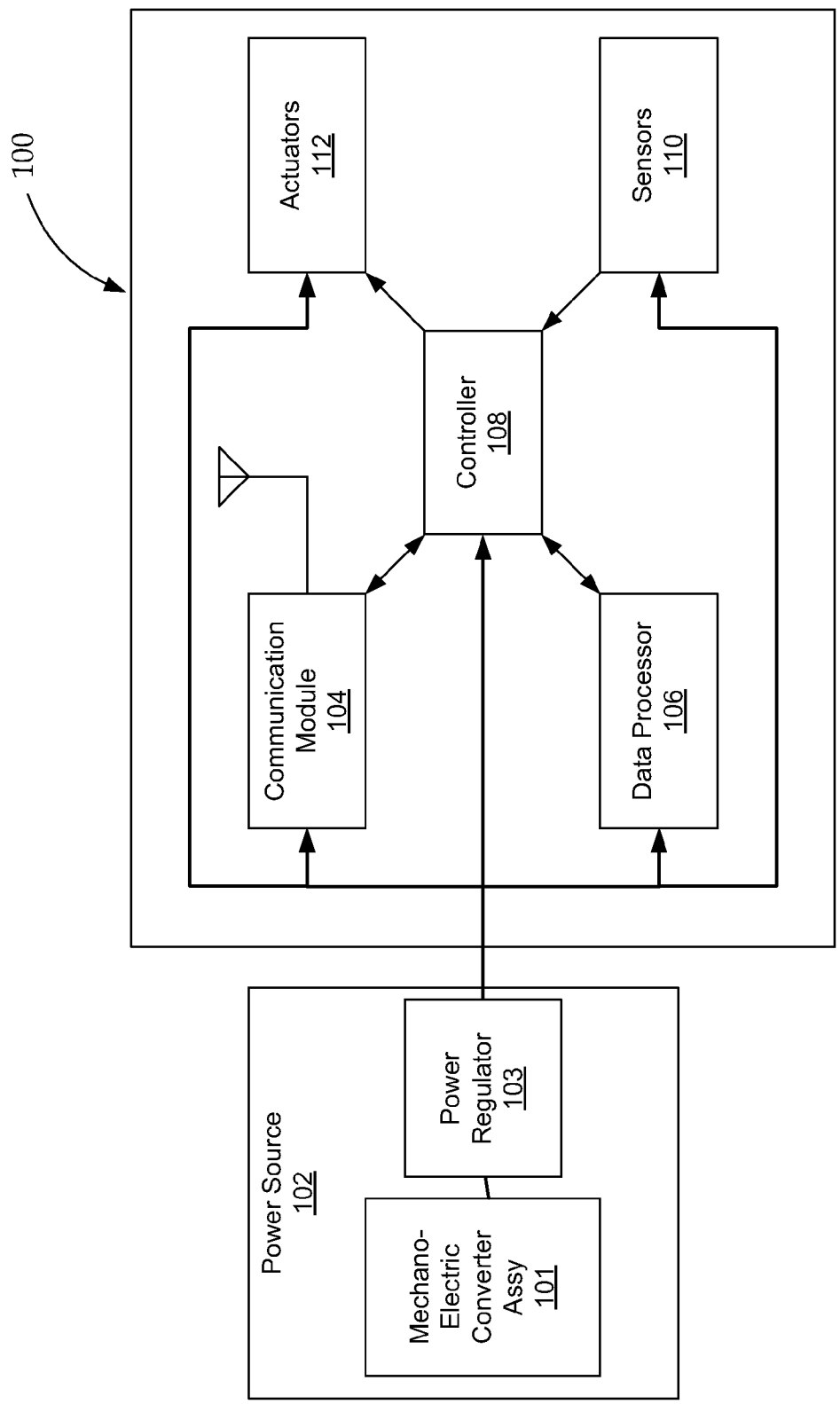
FIG. 1 illustrates a block diagram of an implantable medical device incorporating a subcutaneous power source according to the present invention.

FIG. 1 illustrates one aspect of a subcutaneous power source 102 operable to supply electric power to an implantable medical device 100 that collects local medical related data and communicates the received data to an external processing station or is operable to accept commands either from an external or local source. The medical device 100 is configurable to apply signals, i.e., electrical pulses, to the local environment, such as a human heart.

The power output of subcutaneous power source 102 is dependent on the source of the mechanical motion. For example, a larger blood vessel may exhibit a larger change in cross-sectional diameter and may therefore be able to generate more power. Accordingly, output power may range from a few microwatts to milliwatts.

The operation of a typical implantable medical device 100 is supervised by a controller 108. Function blocks supporting the operation of an implantable medical device 100 include a communications block 104 responsible for communicating commands and data with external or other internal resources, a data processor 106 designed to efficiently process algorithms and data specific to the function of the implantable medical device, sensors 110 designed to collect data from the environment, and actuators 112 responsible for applying signals to the environment. The longevity of an implanted medical device 100 generally depends on the length of time the electrically connected subcutaneous power source 102 can meet the operational power needs of the implantable medical device 100.

The subcutaneous power source 102 comprises a mechano-electric transducer 101 that harnesses the intermittent mechanical energy supplied by a particular living tissue, such as a blood vessel, and a power regulator 103 operable to deliver a configurable amount of electric power to medical device 100.

Figure 2A:
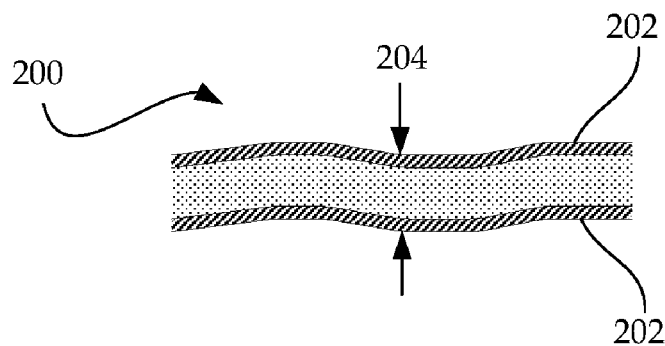
FIGS. 2A, 2B, 2C, and 2D are cross-sectional views of a blood vessel.
Figure 2B:
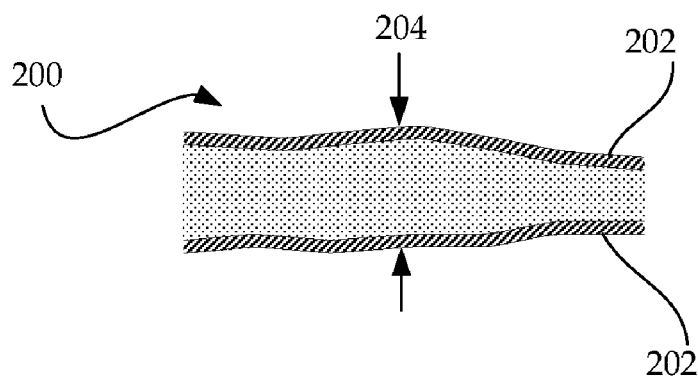
Figure 2C:
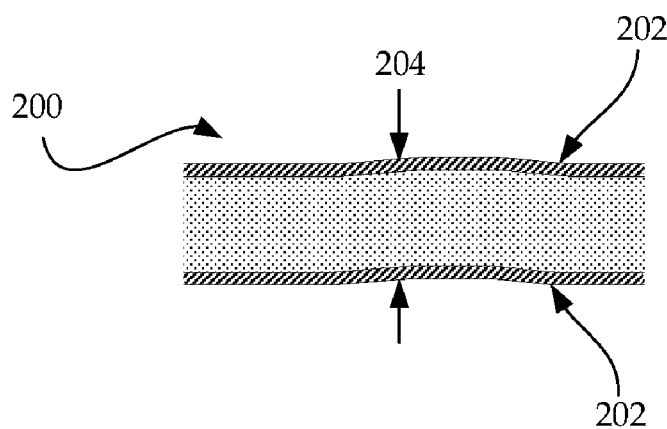

FIGS. 2A-2D illustrate the longitudinal cross-section of a blood vessel 200 during 4 operation states. FIGS. 2A and 2C illustrate the longitudinal cross-section of a blood vessel 200 during the steady diastolic and systolic periods, respectively, of a heart beat. It is this involuntary movement, more specifically, the expansion and contraction of the walls 202 of the blood vessel 200 during a systolic-diastolic blood pressure cycle that is harnessed to produce electric energy delivered to an implanted medical device 100.

Figure 2D:
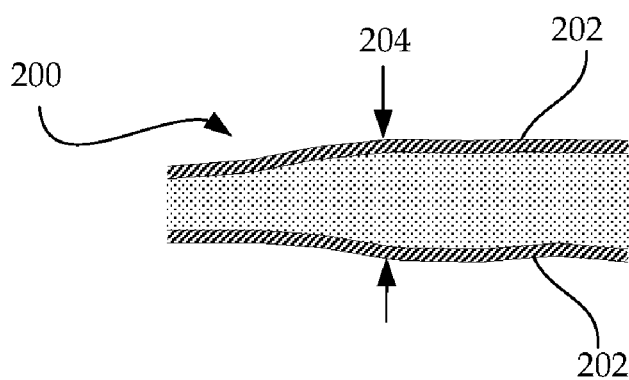

FIGS. 2B and 2D illustrate the change in shape of a blood vessel caused by a leading edge and trailing edge, respectively, of the pressure wave of blood pumped through the vessel by a heart beat. An exemplary embodiment of the invention uses the change in cross section 204 of a blood vessel 200 to generate electrical energy. It is known that the mechanical power of the human heart is about 5 watts (W). In order to take advantage of a portion of this energy without adversely affecting the operation of the human body, a minimal amount is drawn from the mechanical power from the heart to drive one or more medical devices 100.

Figure 3A:
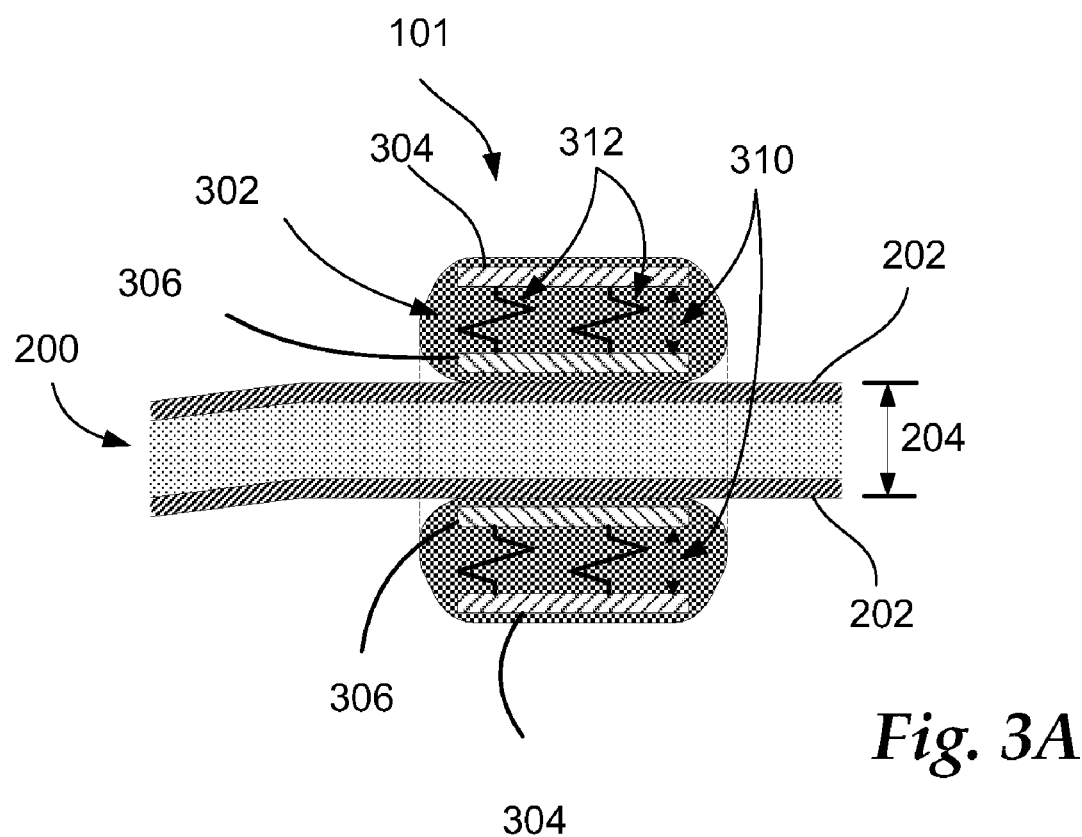
FIGS. 3A and 3B are longitudinal cross-sectional views of an exemplary embodiment of a power source for an implantable medical device.
Figure 3B:
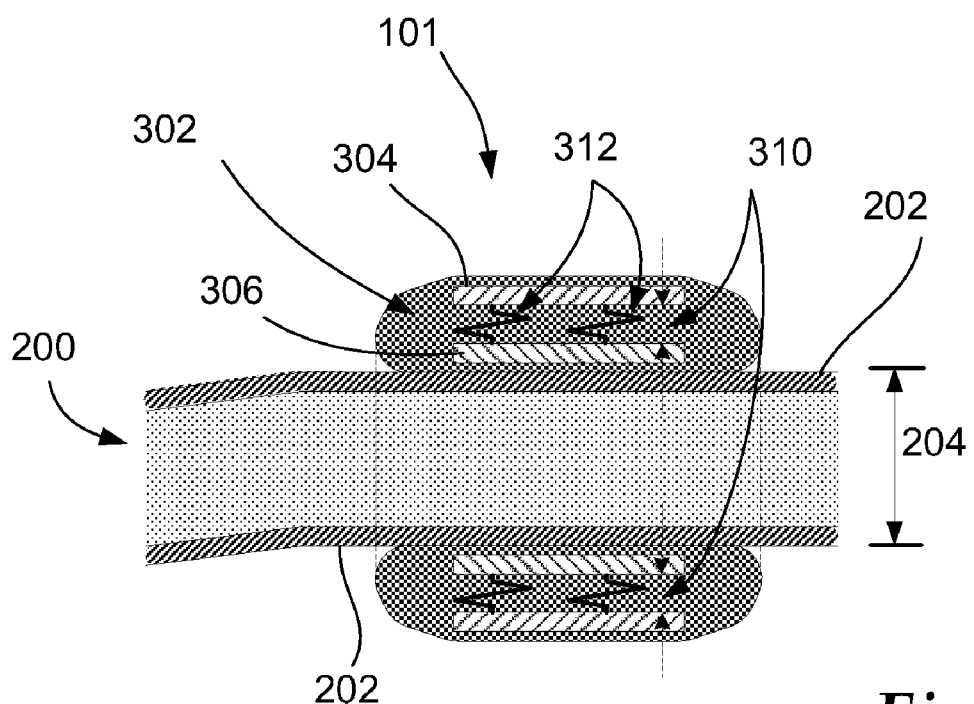
Figure 3C:
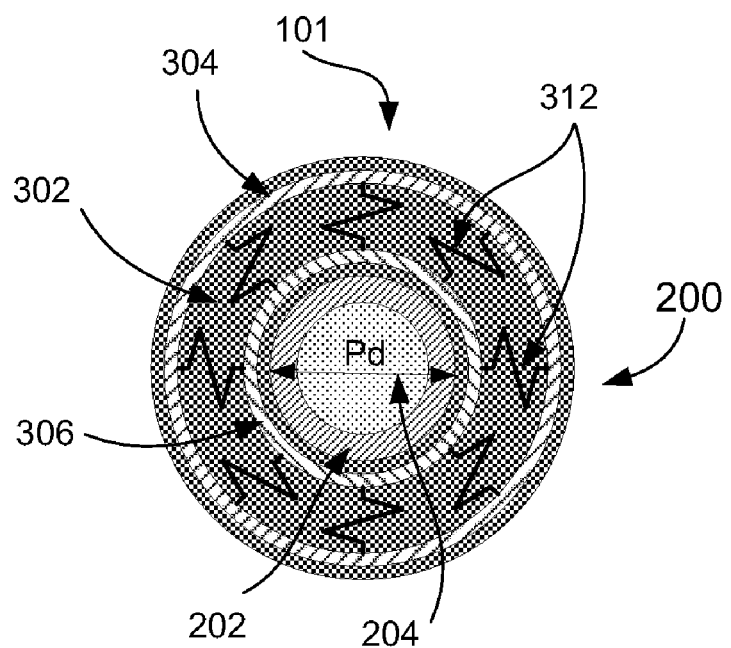
FIGS. 3C and 3D are transversal cross-sectional views of an exemplary embodiment of a power source for an implantable medical device.
Figure 3D:
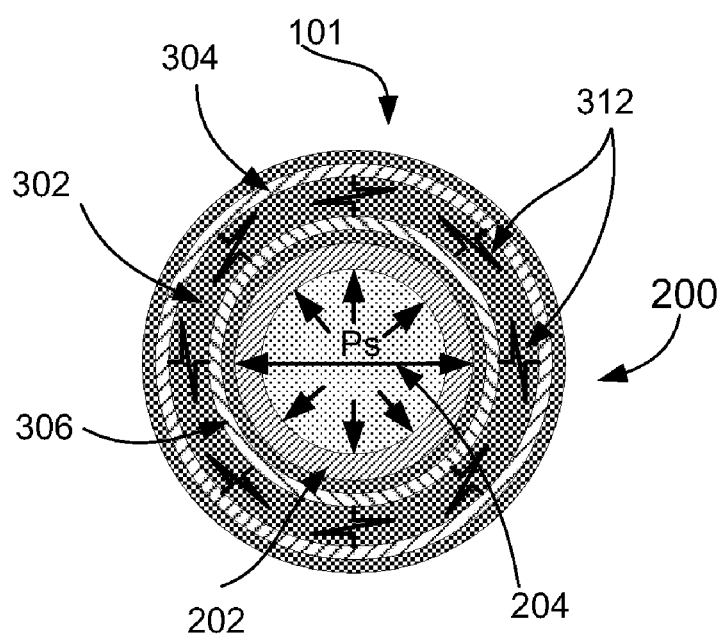

FIGS. 3A and 3B illustrate a longitudinal cross-section of one embodiment of the mechano-electrical transducer assembly 101, and FIGS. 3C and 3D illustrate a transverse cross-section of the same embodiment. Furthermore, as illustrated in FIGS. 3A-3D, the transducer assembly 101 is placed around a blood vessel 200. In this embodiment, transducer assembly 101 comprises an deformable inner element 306, an substantially rigid outer structure 304, and at least one mechano-electric transducer element 312 attached between outer structure 304 and inner element 306, wherein the outer structure 304, the inner element 306, and the mechano-electric transducer element(s) 312 are encased in a biocompatible envelope 302 that can conform to the general shape of blood vessel 200. Inner element 306 is disposed at a position nearest to the outer wall 202 of blood vessel 200 and outer structure 304 is disposed at a position outward of inner element 306. In one embodiment, inner element 306 is an elastic inner structure. In other embodiments, inner element 306 comprises at least one rigid segment, able to expand radially so it can compress or expand a mechano-electric transducer 312 that, in one embodiment, is located between inner element 306 and outer structure 304. In some embodiments at least the transducer 312 is placed inside blood vessel 200. However, external placement is preferred as it reduces the risk of blood clotting and simplifies the associated surgical procedure required to install the power source 102.

FIGS. 3A and 3C illustrate blood vessel 200 during a diastolic period when its cross-section 204 is minimal and a first pressure Pd exerted on an inner surface of vessel wall 202 is at a minimum. Device 101 is configured to apply a minimal pressure on an outer surface of vessel 200 during the diastolic period sufficient to maintain contact with the outside of the vessel wall 202 but insufficient to impede the flow of blood through vessel 200. In some aspects, pressure applied to the outer surface of vessel 200 is derived from one or more mechano-electric transducer elements 312 that include elastic components. Alternatively, the pressure may be supplied by other components, such as springs (not shown). The diameter of outer structure 304 may vary from 1 mm to about 10 mm and depends on the source of the mechanical motion, i.e., the particular blood vessel encased by mechano-electrical transducer assembly 101.

FIGS. 3B and 3D illustrate the blood vessel 200 in a systolic period when its cross-section 204 is at its maximum and blood exerts a second pressure Ps on vessel wall 202. During the expansion of the vessel 200 between its diastolic and systolic phases, the inner element 306 is moved or stretched towards the outer ring 304, compressing the mechano-electric transducers 312. During the expansion of the blood vessel 200, energy is stored in mechano-electric transducer elements 312, responsible for maintaining device 101 in contact with the outer surface of wall 202 of vessel 200. This stored energy is converted into electrical energy by the mechano-electric transducer assembly 101 during the systolic-diastolic contraction of blood vessel 200.

Figure 4A:
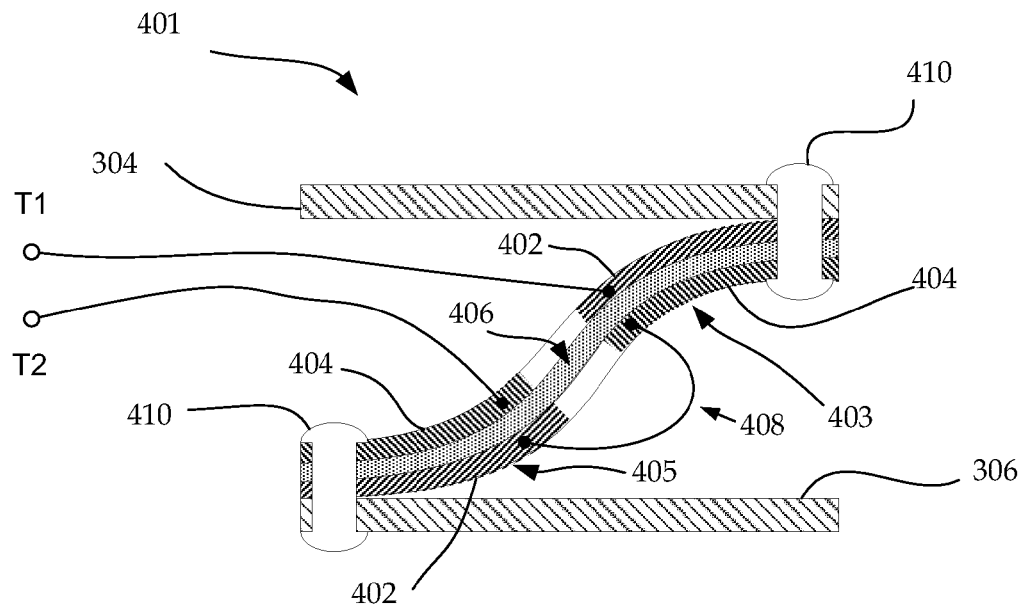
FIGS. 4A and 4B are cross-sectional views of an exemplary mechano-electric transducer embodiment according to the invention.
Figure 4B:
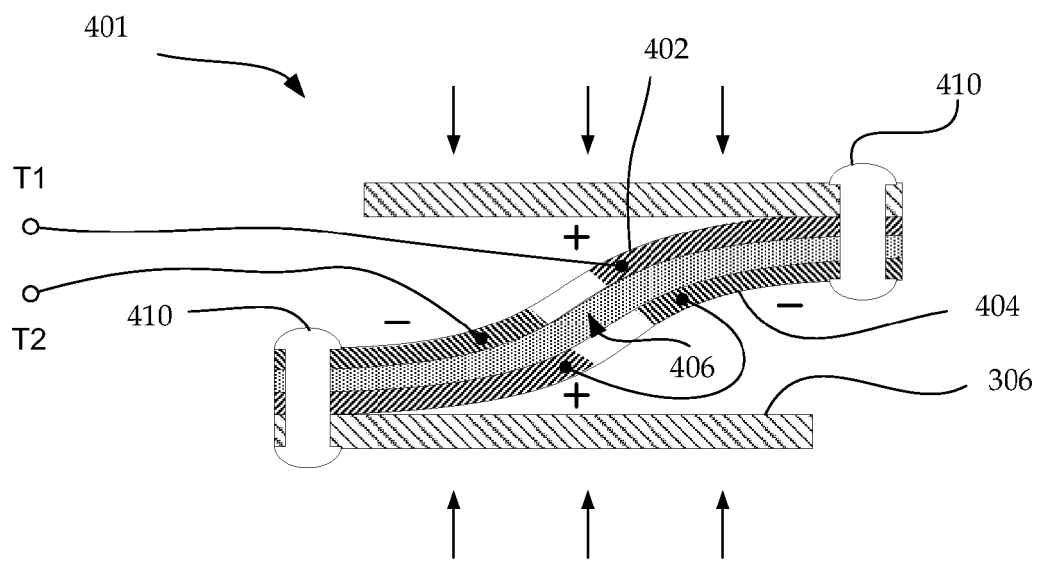

The mechano-electric transducer assembly 401, illustrated in FIGS. 4A and 4B, illustrates an embodiment of the mechano-electric transducer assembly 101 based on piezoelectric effects. Although the transducer assembly 401 illustrates two mechanically coupled bi-layer piezoelectric generators 403 and 405, this number is non-limiting. In contrast to other cantilevered generators, the two bi-layer generators 403, 405 share a common mechanical support 406 onto which piezoelectric layers 402 and 404 are laminated. The two bi-layer generators 403, 405 comprising the mechanical support 406 and piezoelectric layers 402 and 404 are fastened to the outer structure 304 and element 306 by fasteners 410.

During operation inner element 306 is forced by the alternating expanding and contracting blood vessel towards or away from outer element 304 thereby compressing or expanding the piezoelectric assembly 401. Due to the geometry of assembly 401 when piezoelectric layer 402 is compressed, piezoelectric layer 404 stretches, and when layer 402 is stretched, layer 404 compresses. Consequently a first piezoelectric voltage potential generated by mechanical stress on layer 402 is opposite in sign to a second piezoelectric potential generated by mechanical stress on layer 404. The voltage potentials generated by the two piezoelectric generators 403 and 405 may be combined to generate a configurable power output.

Figure 4C:
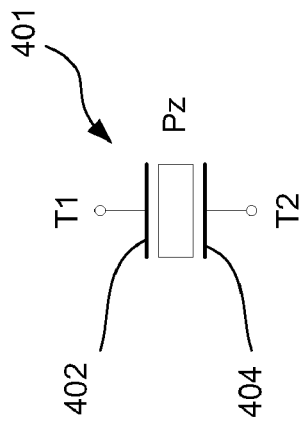
FIG. 4C is a schematic illustrating the exemplary mechano-electric transducer shown in FIGS. 4A and 4B.

For example, FIGS. 4A and 4B illustrate an embodiment wherein the two bi-layer piezoelectric generators 403 and 405 are connected in series by an electrically conducting element 408. It will be understood by those of ordinary skill in the art that other interconnection techniques may also be used in lieu of the series interconnection 408, such as, for example, a parallel interconnection or mixed interconnections among different piezoelectric assemblies. FIG. 4C schematically represents mechano-electric transducer 401, comprises piezoelectric layers 402 and 404, and electrical connectors T1 and T2.

Figure 4D:
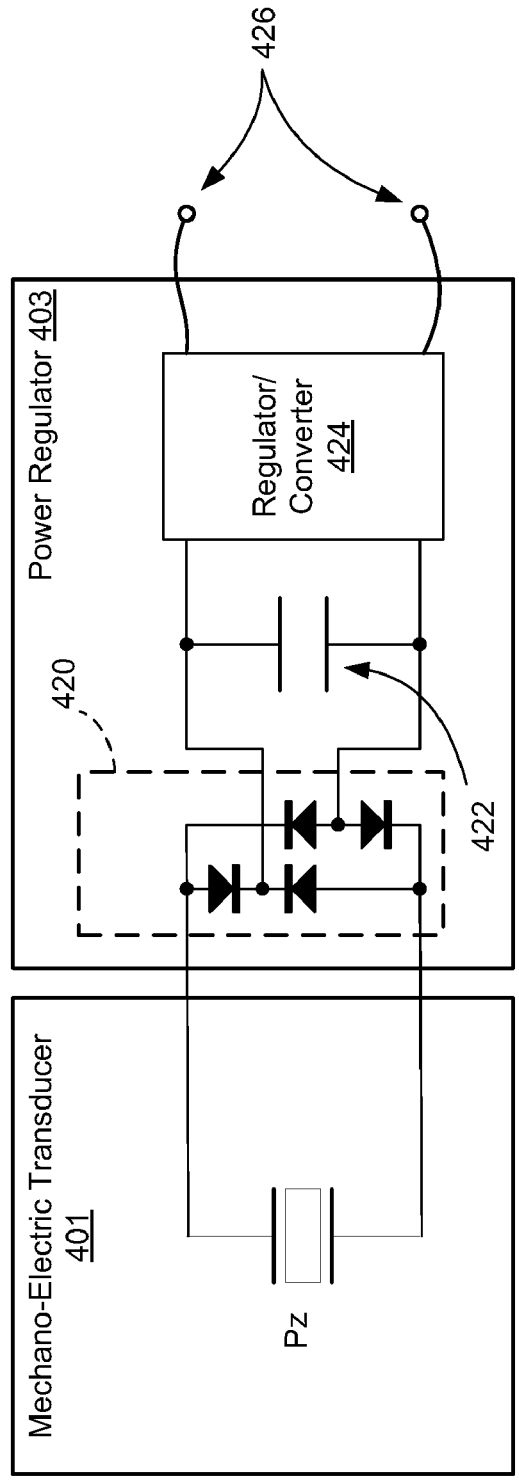
FIG. 4D is a schematic illustrating an exemplary circuit employing the exemplary mechano-electric transducer shown in FIGS. 4A and 4B.

FIG. 4D is a schematic representation of one exemplary power source 402 using the piezoelectric mechano-electric transducer assembly 401 shown in FIGS. 4A and 4B. Because the electrical voltage generated by transducer assembly 401 may be positive or negative, a rectifier 420 is operable to convert an alternating current (AC) output of the transducer assembly 401 into direct current (DC), allowing the electric energy to be stored in a storage element 422, e.g., a charge storage capacitor. In some embodiments, a further conversion is performed by a device, such as voltage regulator/converter 424, to generate an output voltage across terminals 426. The output of the regulator/converter 424 is configurable depending upon specific power requirements of the implanted medical device 100. Non-limiting, the output of regulator/converter 424 may be a constant voltage, a voltage different than the voltage across the storage element 422, a constant current, and etc.

In some embodiments, the output setting of the power source 402 may be used to adjust the amount of energy drawn from the mechanical power of the heart. For example, a lower output power requirement may require the inner element 306 to apply less resistance to the pressures Ps and Pd applied by the pumping action of the heart during the systolic and diastolic stages. In some embodiments, the power source 401 is set to draw a negligible amount of power, e.g., 0.1%, from the mechanical power of the heart.

Figure 5A:
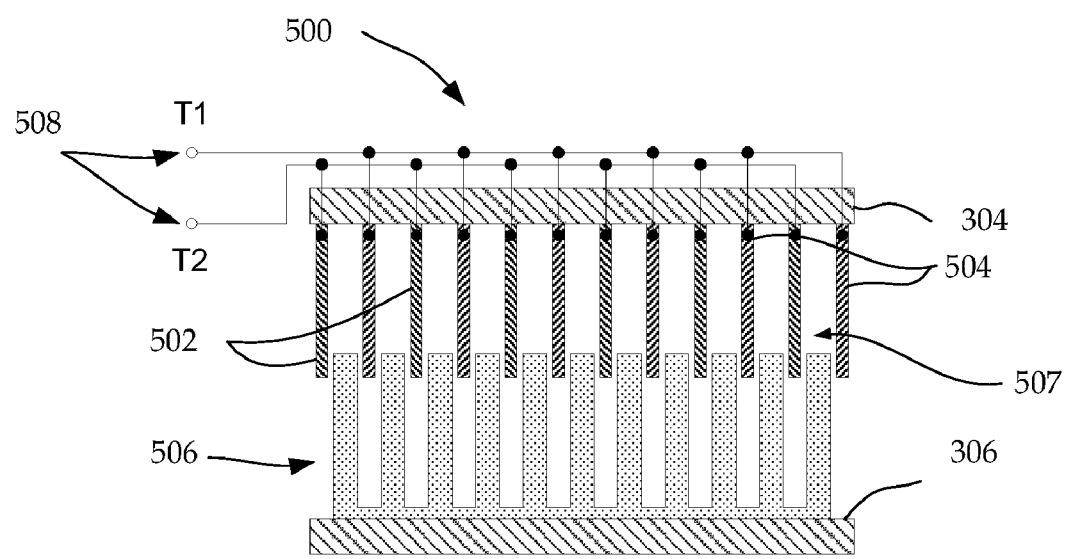
FIGS. 5A and 5B are cross-sectional views of another exemplary mechano-electric transducer embodiment according to the invention.
Figure 5B:
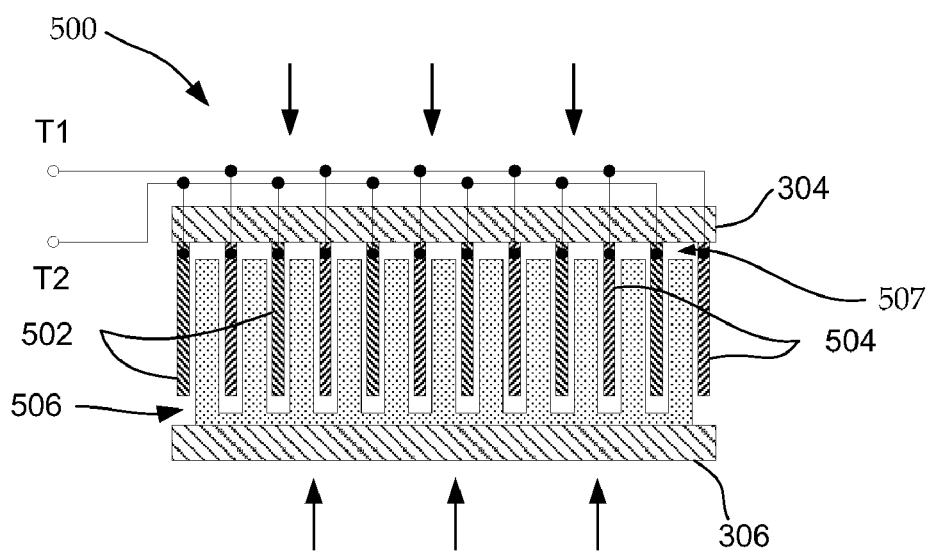

FIGS. 5A and 5B illustrate another embodiment of a mechano-electric transducer. The mechano-electric transducer 500 comprises a multi-plate capacitor including of a first set of conductive plates 502 electrically connected to a first electrical terminal T2 interleaved with a second set of conductive plates 504 electrically connected to a second electrical terminal T1. In order to obtain a high capacitance in the smallest physical space, materials having a high dielectric constant are preferably used. Accordingly, moveable between the plates 502, 504 is a material 506 having a relative high dielectric coefficient to increase the resultant capacitance of the multi-plate capacitor, and therefore increase the output power of the transducer 500. For example, in some embodiments, material 506 includes but is not limited to material such as barium titanate. In other embodiments, a liquid having a high dielectric coefficient may be used.

Furthermore, in some embodiments, the space 507 between the first set of plates 502 and the second set of plates 504 is filled with a movable insulating substance, e.g., air, nitrogen, silicone oil, or any insulating, non-toxic, inert gas or liquid, having a low dielectric coefficient. The movable substance within the space 507 is displaced when the dielectric material is urged to engage conductive plates 502, 504.

The first and second sets of conductive plates 502, 504 are attached to outer structure 304 and dielectric material 506 is in contact with inner element 306. Dielectric material 506 is urged by inner element 306 into the space 507 between the first and second sets of conductive plates 502, 504 by expansion of an encircled blood vessel during the systolic period. Conversely, dielectric material 506 and plates 502, 504 separate during the diastolic period as the dielectric 506 occupies a smaller volume of the space between the first and second sets of plates.

Consequently, due to the mechanical motion of moving the dielectric material 506 relative to conductive plates 502, 504, mechano-electric transducer assembly 500 generates a charging or discharging current and a corresponding voltage across terminals T1 and T2.

In one exemplary embodiment wherein the total area of all conductive plates 502, 504 is approximately one square meter, the spacing between the plates 402, 504 is approximately one micron, and the dielectric material 506 has a relative dielectric coefficient of about 1000 (unitless), then the electric current generated by the system, when the heart beats at a one beat per second rate, is of the order of 0.1 mA at 1V or 0.1 milliwatts.

Figure 5C:
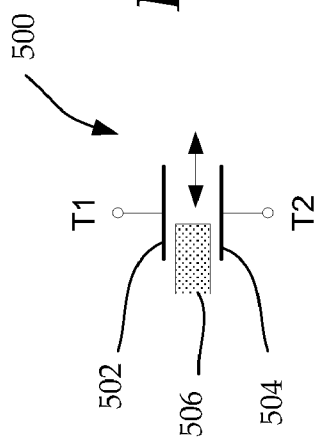
FIG. 5C is a schematic illustrating the exemplary mechano-electric transducer shown in FIGS. 5A and 5B.

FIG. 5C illustrates a symbolic representation of the mechano-electric transducer 500 including the first set of plates 502, the second set of plates 504, and output terminals T1 and T2.

Figure 5D:
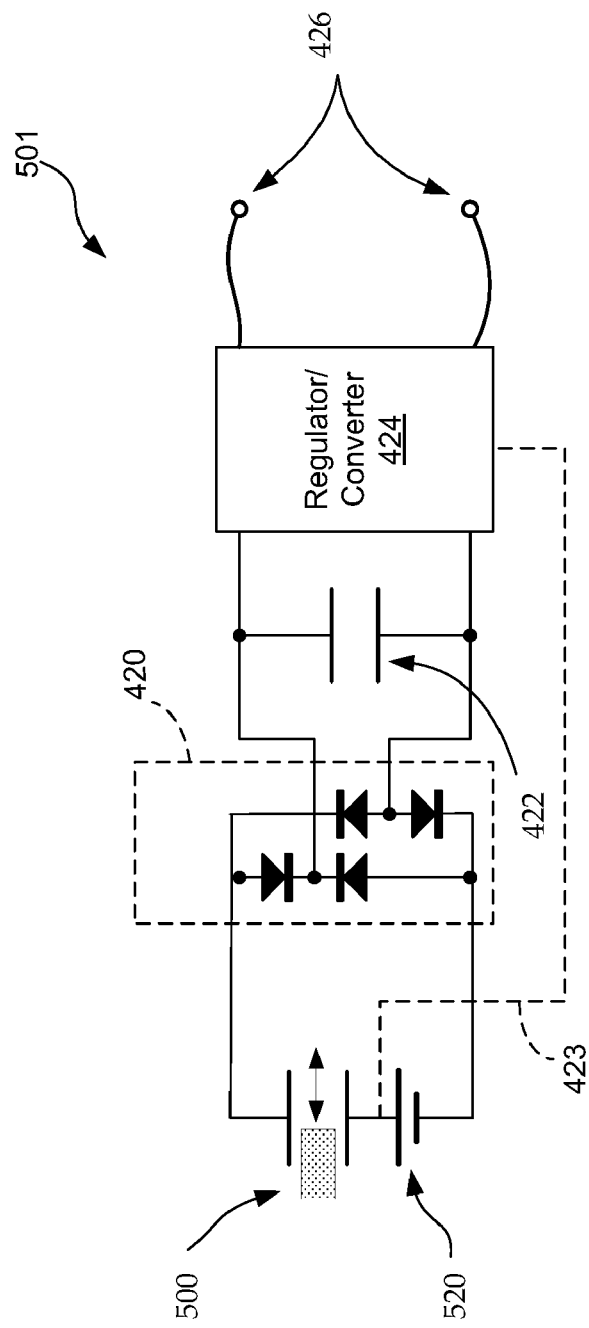
FIG. 5D is a schematic illustrating an exemplary circuit employing the exemplary mechano-electric transducer shown in FIGS. 5A and 5B.

FIG. 5D is a schematic representation of a subcutaneous power source 501 utilizing the mechano-electric transducer assembly 500 illustrated in FIGS. 5A and 5B. The operation of the transducer assembly 500 employs a bias voltage source 520 to provide the electrical voltage potential necessary to charge and discharge the first and second sets of plates 502, 504 of the transducer assembly 500.

Because the polarity of the electrical current generated by the mechano-electric transducer 500 may be positive or negative, a rectifier 420 is provided to convert an alternating current (AC) into direct current (DC). Similar to the circuit of FIG. 4D, the resulting electrical energy is then be stored by a storage element 422, e.g., a capacitor, and the output of the power source 501 is controlled by a regulator/converter device 424.

Because the DC output provided by the bias voltage source 520 is blocked by the capacitive nature of the mechano-electric transducer assembly 500, in some embodiments, the bias voltage source 520 delivers no power to, and is not drained by, the implanted medical device 100. In other embodiments, the bias voltage source may be electrically connected via signal 423 to voltage regulator/converter device 524 to provide backup power in the case of a transducer failure. In other embodiments, the bias voltage source 520 may be replaced by a charged electret layer, not shown, to supply the electric field required by the mechano-electric transducer assembly 500.

Figure 6A:
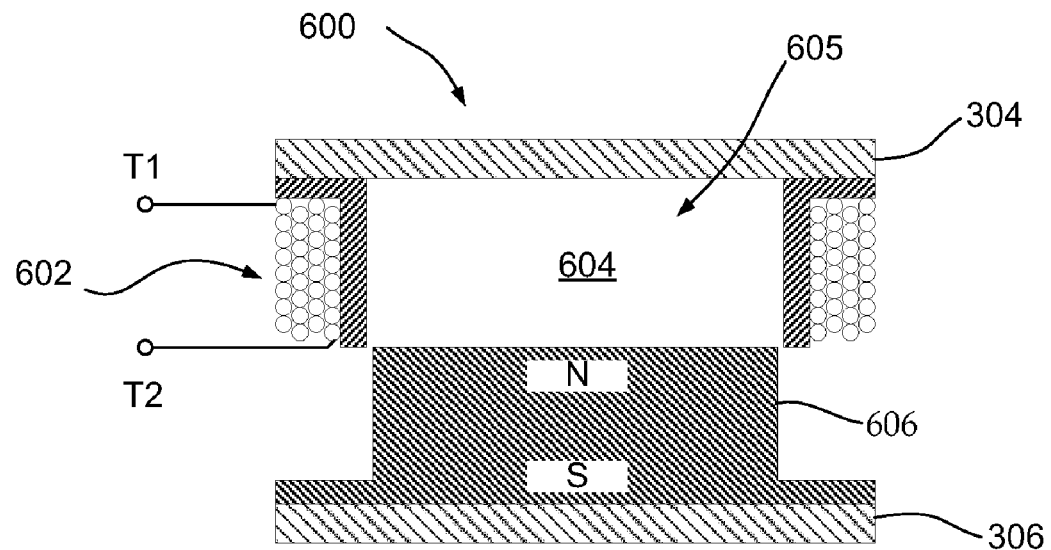
FIGS. 6A and 6B are cross-sectional views of yet another exemplary mechano-electric transducer embodiment according to the invention.
Figure 6B:
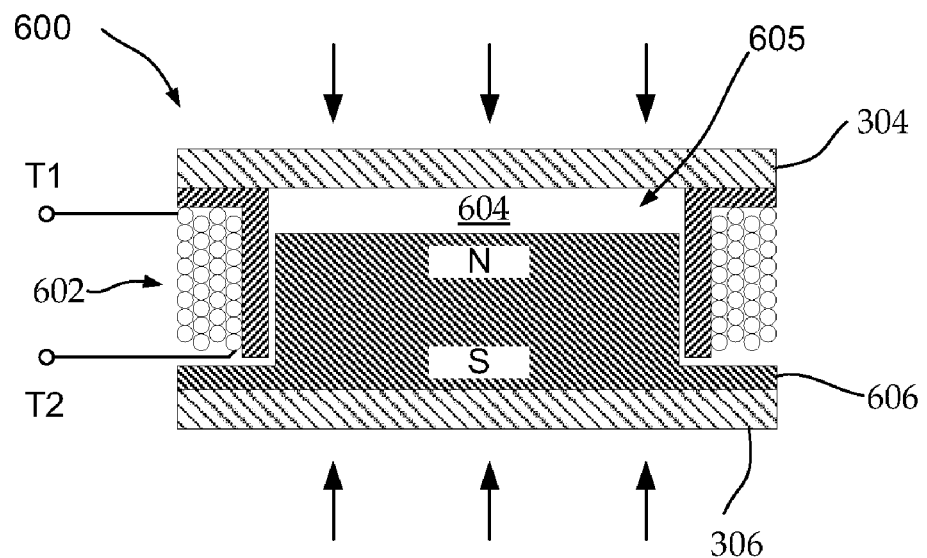

FIGS. 6A and 6B illustrate another embodiment of the mechano-electric transducer assembly 102 of FIG. 1 that includes a substantially linear electromagnetic generator 600. Electromagnetic generator 600 comprises a coil winding 602 attached to the outer structure 304, and a magnetized core 606 having a north pole, N, and a south pole, S. Core 606 is attached to inner element 306 and is movable within a core space 604 central to the coil winding 602. Non-limiting, the core space 604 is filled with a non-magnetic fluid material 605, such as silicone oil. FIG. 6A illustrates the diastolic phase of a systolic-diastolic cycle, wherein the magnetic core 606 is substantially removed from the core space 604. FIG. 6B illustrates the systolic phase wherein the relative movement of the inner element 306 with respect to the outer structure 304 urges the magnetized core 606 within the core space 604 thereby inducing a current within the coil winding 602. FIG. 6C shows a symbolic representation of the mechano-electric transducer 600, shown in FIGS. 6A and 6B.

FIG. 6D is a schematic representation of a subcutaneous power source 601 using the electromagnetic generator 600 shown in FIGS. 6A and 6B. With reference to FIG. 6D, the operation of the electromagnetic generator 600 requires the use of a matching transformer 620 that adapts, e.g., matches, the impedance of the mechano-electric transducer 600 to the impedance of the implanted medical device 100. Similar to the power source illustrated in FIGS. 4D and 5D, a rectifier 420, a storage element 422, and a regulator/converter 424 are provided.

Figure 7A:
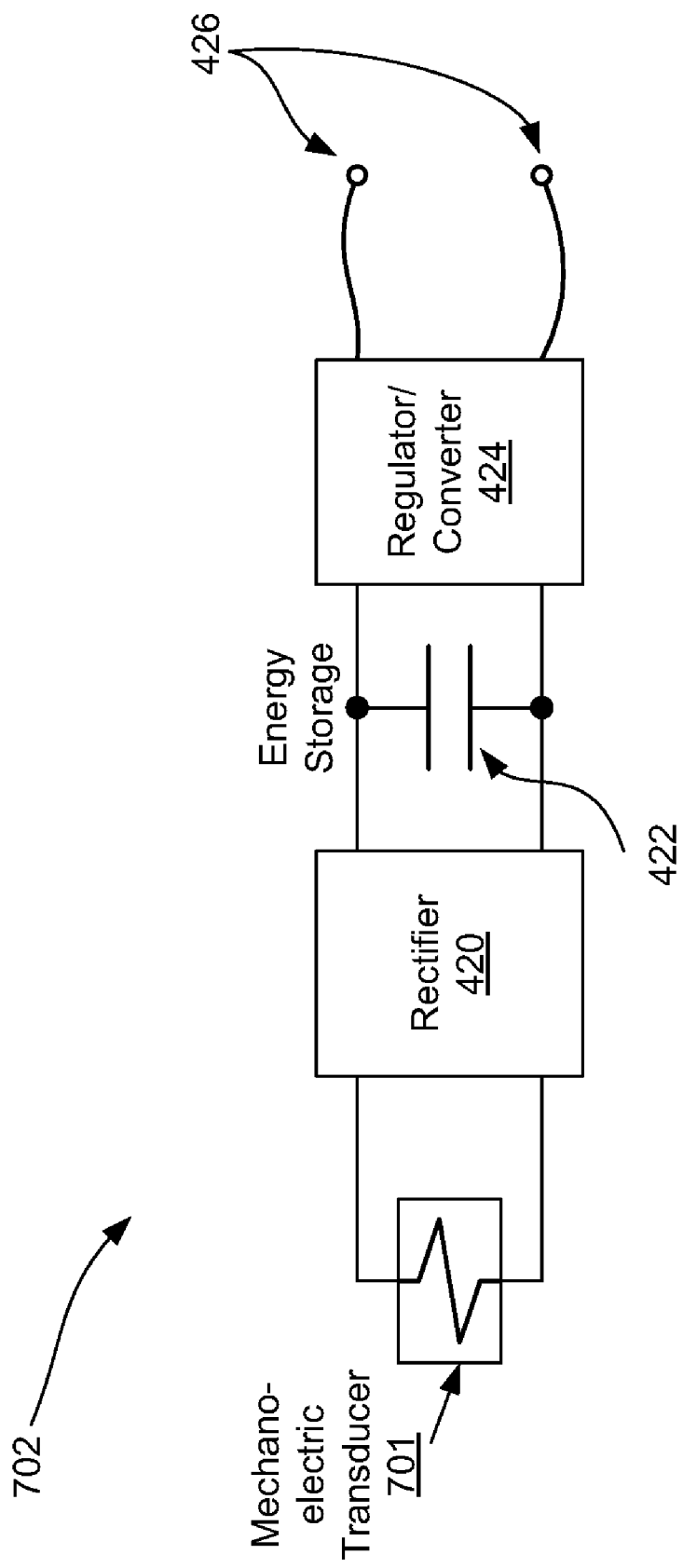

FIG. 7A depicts a schematic diagram of one embodiment of subcutaneous power source 702 using a mechano-electric transducer 701. Non-limiting, mechano-electric transducer 701 uses piezoelectric, electric, electromagnetic or other principles for converting mechanical motion into electricity. In some embodiments it is desirable to connect multiple mechano-electric transducers 701 in parallel to combine their respective output currents prior to rectification by rectifiers 420, as illustrated in FIG. 7B. In other embodiments multiple mechano-electric transducers 701 are connected in series to combine their output voltages as illustrated in FIG. 7C.

The connection of multiple mechano-electric transducers 702 in series, or in parallel, is possible because of their synchronous nature. In other words, all the mechano-electric transducers 702 are compressed or expanded at the same time, thereby generating voltages or currents of the same polarity. The connection of mechano-electric transducers 702 in series or parallel provides further benefits by simplifying the application circuits for various embodiments of the invention.

Figure 8A:
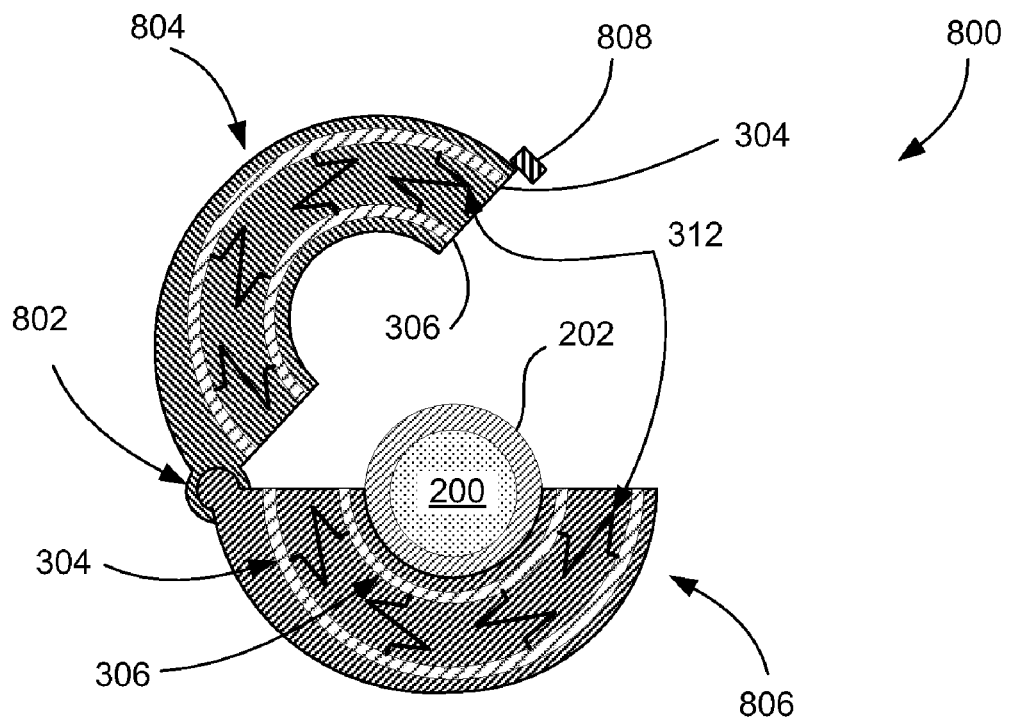
FIGS. 8A and 8B are cross-sectional views of another exemplary embodiment of a mechano-electric transducer according to the invention.
Figure 8B:
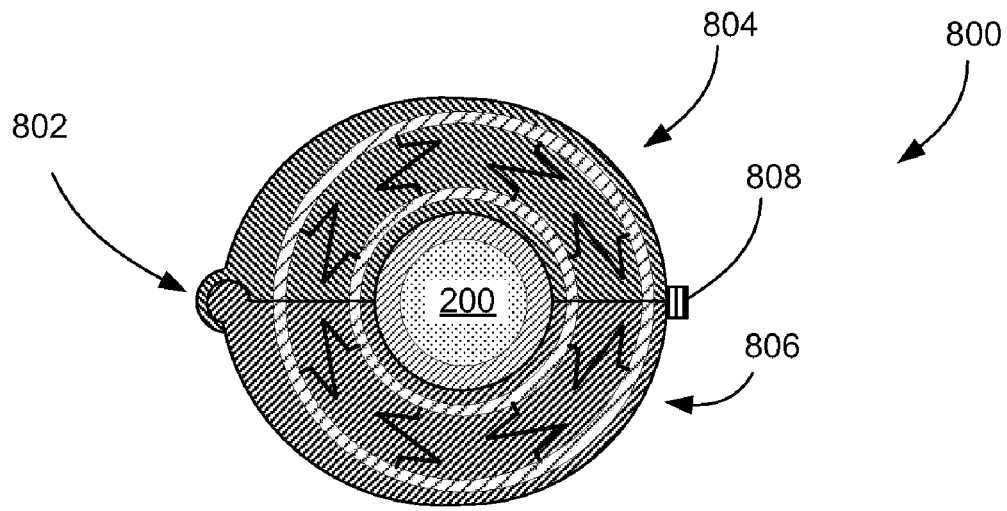

FIGS. 8A and 8B depict yet another embodiment of mechano-electric transducer 101 and comprises at least two substantially similar subassemblies 804, 806 mechanically connected together through mobile joining mechanisms 802, such as, for example hinges, elastic elements, etc. When closed around a blood vessel 200, the subassemblies 804 and 806 maintain their position using a securing mechanism 808. Non-limiting, securing mechanism 808 includes, for example, a latch, a lock, a spring and other known securing mechanisms. The structure of each subassembly 804, 806 is substantially similar to the structure of the device 301 shown in FIGS. 3A and 3B, and the electrical power produced by the subassemblies 804, 806 may in some embodiments be cumulatively added to increase the electric output power of the power source. Because the mechano-electric transducer is segmented into subassemblies 804, 806, installation around a wall 202 of blood vessel 200 is easily accomplished.

While the foregoing disclosure shows illustrative aspects and/or embodiments, it should be noted that various changes and modifications could be made herein without departing from the scope of the described aspects and/or embodiments as defined by the appended claims. Furthermore, although elements of the described embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

In particular, the type, number, and overall size of the mechano-electric transducers, including the materials, structural dimensions, and configurations of the subcutaneous power source may vary depending on the specific medical device 100 or devices powered by the power source.

The various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The data processor 106 of FIG. 1 may be implemented using a microprocessor, but, in the alternative, the processor may be any conventional processor, controller, microcontroller, or state machine. The processor 106 may also be implemented as a combination of computing devices, e.g., a combination of a DSP and a microprocessor, a plurality of microprocessors, one or more microprocessors in conjunction with a DSP core, or any other such configuration.

Further, the steps and/or actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, or any other form of storage medium known in the art. An exemplary storage medium may be coupled to the processor, such that the processor can read information from, and write information to, the storage medium. In the alternative, the storage medium may be integral to the processor. Further, in some aspects, the processor and the storage medium may reside in an ASIC. Additionally, in some aspects, the steps and/or actions of a method or algorithm may reside as one or any combination or set of instructions on a machine readable medium and/or computer readable medium.

What is claimed is:

1. A method of generating electric power for subcutaneously implanted devices, comprising:
    encircling a blood vessel with a mechano-electric transducer; and
    converting mechanical energy generated from an expansion and contraction of a blood vessel to electric energy.

2. The method of claim 1, wherein converting mechanical energy generated from an expansion and contraction of a blood vessel includes capturing involuntary mechanical movement of an elastic expansion and contraction of blood vessels during systolic-diastolic cycles.

3. The method of claim 1, wherein converting mechanical energy to electric energy includes urging an inner element towards an outer structure, wherein the inner element is disposed so as to be in close proximity to an outer surface of the blood vessel.

4. The method of claim 1, wherein converting mechanical energy to electric energy includes stimulating at least one piezoelectric generator.

5. The method of claim 1, wherein converting mechanical energy to electric energy includes actuating an electromagnetic transducer.

6. The method of claim 1, wherein converting mechanical energy to electric energy includes actuating a variable capacitor electric generator.

7. The method of claim 6, wherein converting mechanical energy to electric energy includes:
    moving a dielectric material within a space between a first and second set of conductive plates; and
    generating a charging or discharging current and a respective voltage across a pair of terminals connected to the first and second set of conductive plates.

8. A power source for converting mechanical power into electrical power comprises at least one mechano-electric transducer assembly mechanically coupled to involuntarily moving tissue, the mechano-electric transducer assembly including:
    a deformable inner elastic structure configured to expand in response to an expansion of a blood vessel;
    a substantially rigid outer structure positioned outward of the inner element;
    a mechano-electric transducer element disposed between the substantially rigid outer structure and the inner element, the mechano-electric transducer element operable to generate electric energy and output the electric energy to a pair of output terminals; and
    a deformable biocompatible envelope encasing the outer structure, the inner element and the mechano-electric transducer element;
        wherein the inner element is operable to expand outward towards the outer structure during a systolic period, the expansion of the inner element operable to cause the mechano-electric transducer element to generate electricity.

9. The device of claim 8, wherein the mechano-electric transducer assembly is operable to convert mechanical energy into electrical energy by a piezoelectric effect.

10. The device of claim 9, wherein the mechano-electric transducer element includes at least one pair of mechanically coupled piezoelectric generators, each having two piezoelectric layers and a shared mechanical support onto which each of the piezoelectric layers are laminated.

11. The device of claim 8, wherein the mechano-electric transducer assembly is operable to convert mechanical energy into electrical energy based upon a piezomagnetic effect.

12. The device of claim 8, further comprising an electric storage component including a changeable geometry operable to convert the mechanical energy into electrical energy by changing the geometry of the electrical energy storage component.

13. The device of claim 8, wherein the mechano-electric transducer assembly is operable to convert mechanical energy into electrical energy by driving at least one variable capacitor electric generator.

14. The device of claim 8, wherein the mechano-electric transducer assembly is operable to convert mechanical energy into electrical energy by driving at least one electromagnetic generator.

15. The device of claim 8, wherein the mechano-electric transducer element comprises:
   a multi-plate capacitor including of a first set of conductive plates a second set of conductive plates interleaved in a non-contacting configuration that includes spaces between the first and second sets of plates; and
   a material having a high dielectric coefficient movable between the spaces formed between the first and second sets of plates.

16. The device of claim 15, wherein the mechano-electric transducer element further comprises an insulating substance having a low dielectric coefficient essentially filling the space between the first set of plates and the second set of plates in the absence of the high dielectric coefficient material.

17. The device of claim 15, wherein:
   the first set of plates and the second set of plates are attached to the outer structure; and
   the high dielectric coefficient material is mechanically engaged by the inner element;
   whereby the high dielectric coefficient material is urged by the inner element to occupy the space between the first and second sets of plates by an expansion of an encircled blood vessel during a systolic period.

18. The device of claim 8, further comprising:
   a linear electromagnetic generator including a coil winding attached to the outer structure; and
   a core comprising magnetic material attached to the inner element and movable within a core space central to the coil winding;
   whereby the core is urged by the inner element to occupy the core space by an expansion of an encircled blood vessel during a systolic period.

19. The device of claim 8, wherein a plurality of mechano-electric transducer assemblies are wired together and are configured to increase an amount of electric energy produced by the device.

20. The device of claim 8, further comprising a configurable voltage regulator/converter module operable to generate at least one of a constant voltage and a constant current output.

21. The device of claim 8, further comprising an electrically connectable medical device.

22. A device for converting mechanical power into electrical power comprising at least one mechano-electric transducer assembly arranged to be mechanically coupled to involuntarily moving tissue, the mechano-electric transducer assembly includes:
   a substantially rigid outer structure;
   a deformable inner element;
   a mechano-electric transducer element disposed between the substantially rigid outer structure and the inner element, the mechano-electric transducer element operable to generate electric energy and output the electric energy to a pair of output terminals; and
   a deformable biocompatible envelope substantially surrounding the outer structure, the inner element and the mechano-electric transducer element;
   wherein the inner element is operable to apply a predetermined pressure on a substantially surrounded blood vessel during a diastolic period and to expand outward towards the outer structure during a systolic period, the expansion of the inner element operable to cause the mechano-electric transducer element to generate electricity; and
   wherein the mechano-electric transducer element includes:
      a multi-plate capacitor including of a first set of conductive plates interleaved with a second set of conductive plates; and
      a high dielectric coefficient material movable within a space between the first and second sets of plates.

* * * * *